(12) United States Patent
Dong et al.

(10) Patent No.: US 11,493,438 B2
(45) Date of Patent: Nov. 8, 2022

(54) METHANE VALUE ONLINE REAL-TIME MONITORING SYSTEM

(71) Applicant: Harbin Engineering University, Harbin (CN)

(72) Inventors: Quan Dong, Harbin (CN); Yuqin Zhang, Harbin (CN); Di Wang, Harbin (CN); Changhao Lu, Harbin (CN); Zuo Ni, Harbin (CN); Xiyu Yang, Harbin (CN)

(73) Assignee: Harbin Engineering University, Harbin (CN)

( * ) Notice: Subject to any disclaimer, the term of this patent is extended or adjusted under 35 U.S.C. 154(b) by 0 days.

(21) Appl. No.: 17/203,893

(22) Filed: Mar. 17, 2021

(65) Prior Publication Data

US 2021/0199573 A1    Jul. 1, 2021

(30) Foreign Application Priority Data

Mar. 21, 2020   (CN) .......................... 202010204328.0

(51) Int. Cl.
  *G01N 21/39* (2006.01)
  *G01N 33/00* (2006.01)

(52) U.S. Cl.
  CPC ......... *G01N 21/39* (2013.01); *G01N 33/0036* (2013.01)

(58) Field of Classification Search
  CPC ........................... G01N 21/39; G01N 33/0036
  See application file for complete search history.

(56) References Cited

U.S. PATENT DOCUMENTS

| | | | | |
|---|---|---|---|---|
| 6,091,492 A | * | 7/2000 | Strickland | .......... G01N 15/0211 356/336 |
| 2003/0043364 A1 | * | 3/2003 | Jamieson | .............. G01S 7/4817 356/28.5 |
| 2012/0154813 A1 | * | 6/2012 | Li | ............................ F02C 9/26 451/1 |
| 2015/0241399 A1 | * | 8/2015 | Li | ...................... G01N 33/0036 73/23.31 |
| 2016/0244685 A1 | * | 8/2016 | Grossman | ............... C10L 3/101 |

FOREIGN PATENT DOCUMENTS

CN     207379917 U   *   5/2018   ............. G01N 21/39

* cited by examiner

*Primary Examiner* — Jamil Ahmed
(74) *Attorney, Agent, or Firm* — IPro, PLLC; Na Xu

(57) ABSTRACT

The disclosure discloses a methane value online real-time monitoring system, which includes a laser tunable system portion, a gas component detection system portion and a data processing system portion. The laser tunable system portion includes a computer, laser drivers, tunable lasers, a laser beam combiner, a collimator, and a beam expander, which are connected in sequence. The gas component detection system portion includes a gas supply system pipeline, a hose, a valve, and a gas chamber. The data processing system portion includes a detector, lock-in amplifiers, an oscilloscope, and a data acquisition card, which are connected in sequence. In a working process of the methane value online real-time monitoring system, gas mass namely the methane value change can be monitored in real time on line by collecting natural gas introduced into a combustion chamber through a gas supply system pipeline of a natural gas engine.

3 Claims, 3 Drawing Sheets

METHANE VALUE ONLINE REAL-TIME MONITORING SYSTEM

TECHNICAL FIELD

The disclosure relates to the field of gas fuel engines, and in particular to a system for online real-time monitoring of a natural gas methane number.

BACKGROUND

The call for energy conservation and environmental protection is increasing in the world today, the requirements of emission regulations are strict increasingly, and energy conservation and emission reduction have become one of the key points in the development of internal combustion engine industry. Gas-fueled internal combustion engines have received more and more attention due to their good thermal efficiency and low emission characteristics. With the development of natural gas engines in China, studies on the natural gas engines are getting deeper. The studies have shown that the methane number is an important indicator to characterize the anti-knock performance of internal combustion engines, the natural gas with high methane number (80-90) may provide smooth combustion from spark ignition, while the natural gas with low methane number (55-65) increases the risk of knocking in some parts of a combustion chamber through auto-ignition. Knocking results in that a piston inside an engine knocks a cylinder, the power of the engine is reduced, the temperature rises, the load and wear of internal parts of the engine are increased, the formation of carbon deposits inside the engine is increased, the internal parts of the engine are deformed due to the temperature rise and the like. Various hazards caused by knocking are undesirable, and there is a need for a system capable of monitoring an indicator characterizing the anti-knock performance, namely, methane number in real time online.

SUMMARY

In order to solve the knocking problem related to rapid change of gas mass, the disclosure provides an online real-time non-contact methane number monitoring system that is high in precision and rapid in reaction.

The disclosure is implemented in the following way:

A methane number online real-time monitoring system includes a laser tuning system, a gas component detection system and a data processing system. The laser tuning system includes a computer, laser drivers, tunable lasers, a laser beam combiner, a collimator, and a beam expander, which are connected in sequence. The gas component detection system includes a gas supply system pipeline, a hose, a valve, and a gas chamber, the gas supply system pipeline is connected with the gas chamber through the hose, and the valve is arranged on the hose. The data processing system includes a detector, lock-in amplifiers, an oscilloscope, and a data acquisition card, which are connected in sequence. One end of the gas chamber is connected with the beam expander, and the other end is connected with the detector. One end of the computer is connected with the laser drivers, and the other end is connected with the data acquisition card.

The tunable lasers include a methane laser, an ethane laser, a propane laser, a butane laser, a carbon dioxide laser, and a nitrogen laser.

The tunable lasers and the laser drivers are in one-to-one correspondence.

The disclosure has the following beneficial effects:

In a working process of the methane number online real-time monitoring system, gas mass namely the methane number change can be monitored in real time online by collecting natural gas introduced into a combustion chamber through a gas supply system pipeline of a natural gas engine, and the knocking problem related to rapid change of the gas mass is solved. The whole system is easy to operate, low in cost, high in severe environment adaptability, low in maintenance cost, safe, free of pollution, capable of achieving real-time measurement, high in reliability and the like.

In the figures: 1, computer; 2, laser driver; 3, tunable laser; 4, laser beam combiner; 5, collimator; 6, beam expander; 7, gas supply system pipeline; 8, valve; 9, plastic hose; 10, gas chamber; 11, detector; 12, lock-in amplifier; 13, oscilloscope; 14, data acquisition card.

DETAILED DESCRIPTION

The disclosure will be described below in detail with reference to the accompanying drawings and specific examples.

Figure 1:
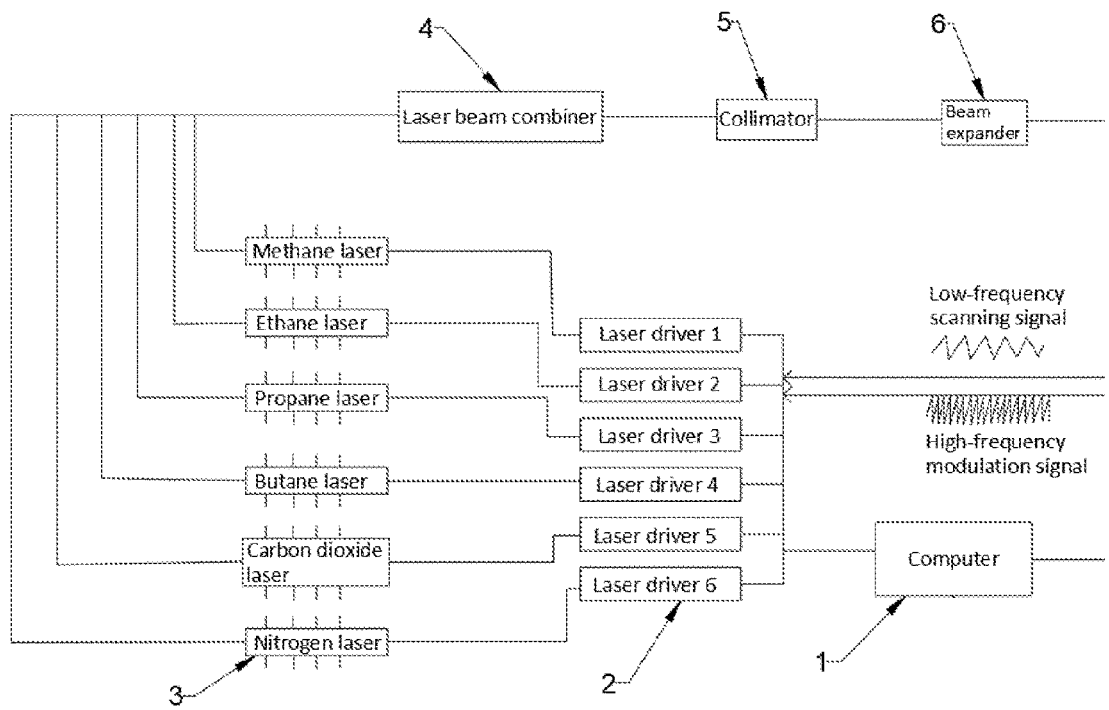
FIG. 1 shows a laser tuning system of a methane number online real-time monitoring system according to the disclosure.
Figure 2:
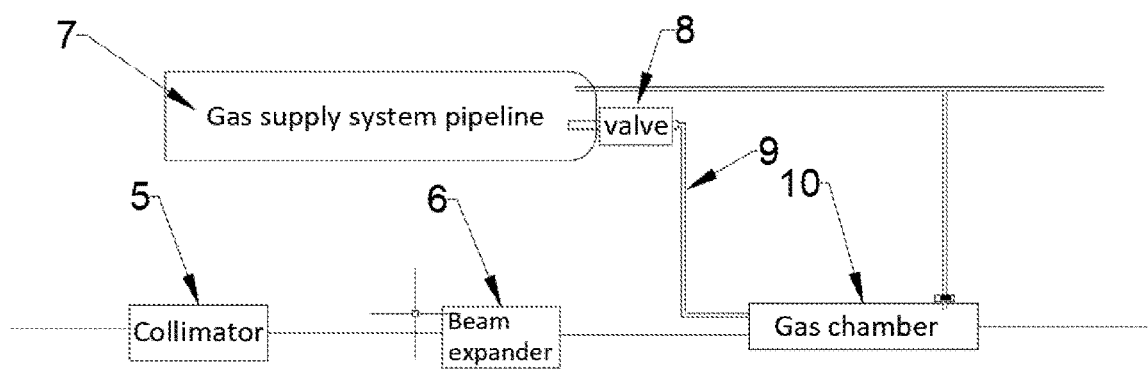
FIG. 2 shows a gas component detection system of a methane number online real-time monitoring system according to the disclosure.
Figure 3:
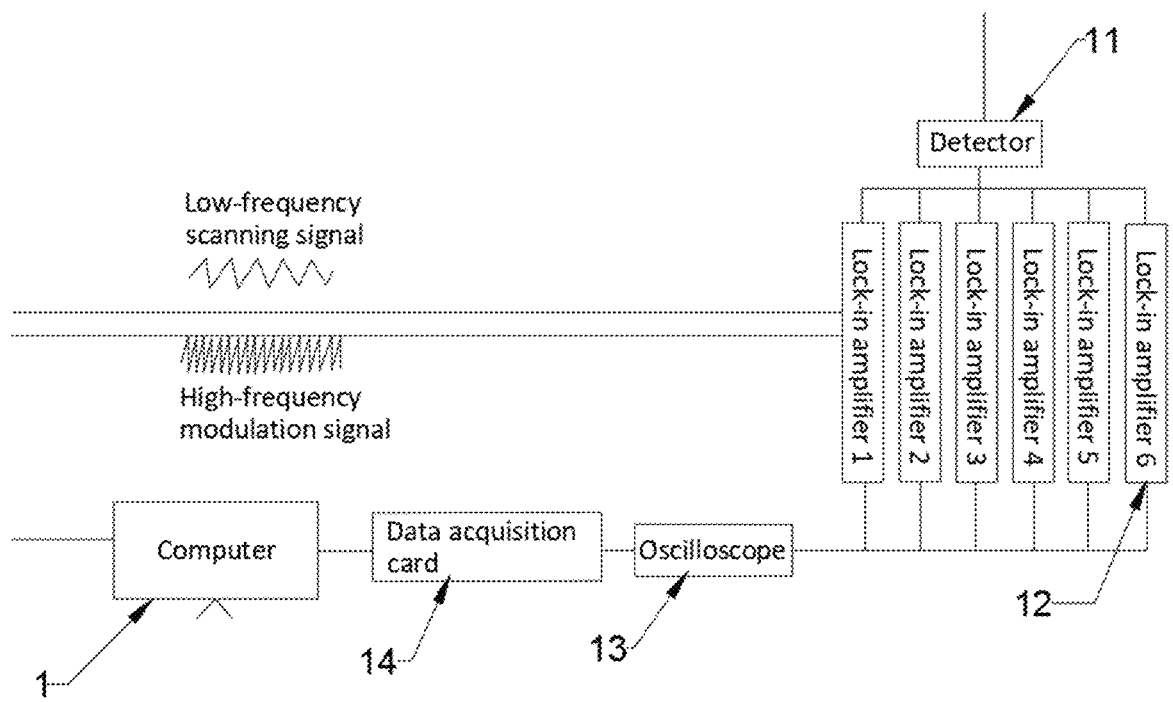
FIG. 3 shows a data processing system of a methane number online real-time monitoring system according to the disclosure.
Figure 4:
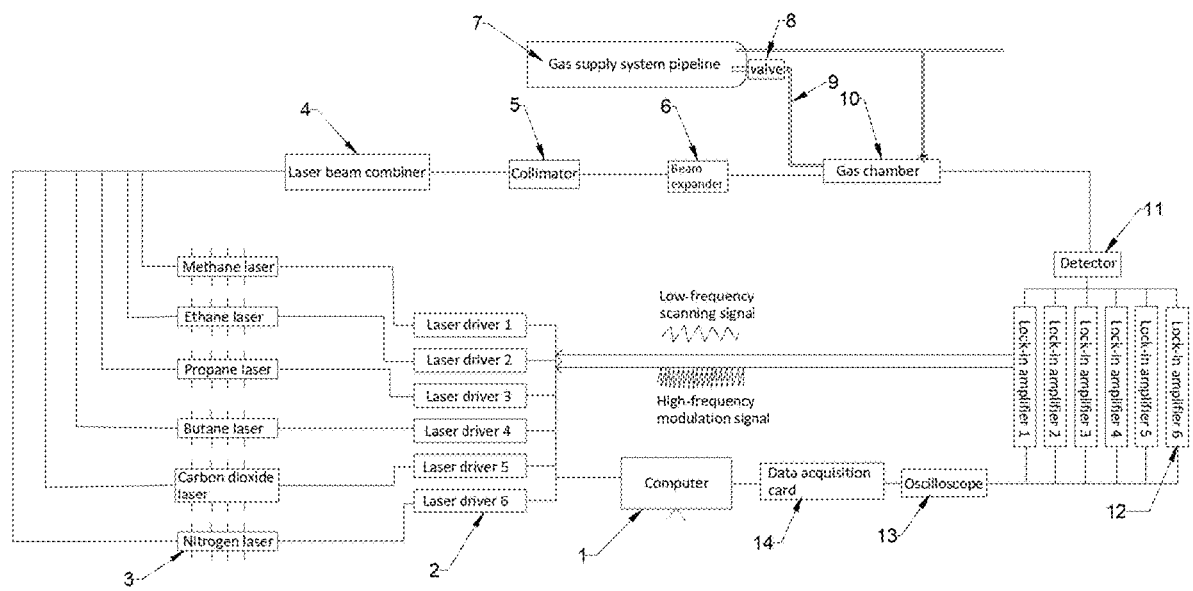
FIG. 4 is a general layout diagram of a methane number online real-time monitoring system according to the disclosure.

FIG. 1, FIG. 2 and FIG. 3 show three portions of a methane number online real-time monitoring system according to the disclosure. 1, computer; 2, laser driver; 3, tunable laser; 4, laser beam combiner; 5, collimator; 6, beam expander; 7, gas supply system pipeline; 8, valve; 9, plastic hose; 10, gas chamber; 11, detector; 12, lock-in amplifier; 13, oscilloscope; 14, data acquisition card. FIG. 2 shows a gas component detection system. Natural gas inside a gas supply system pipeline is firstly filled into a gas chamber after passing through a valve of the gas supply system pipeline through a plastic hose. FIG. 1 shows a laser tuning system. It can be seen from the figure that a methane laser, an ethane laser, a propane laser, a butane laser, a carbon dioxide laser, and a nitrogen laser are respectively controlled by respective laser drivers. Firstly, different lasers are tuned to respective detection gas sensitive wavelengths through the following specific operation: the tuning of the wavelengths is controlled by temperature and current, the temperature achieves coarse tuning, while the current achieves fine tuning; the temperature is firstly tuned, an approximate wavelength of a gas absorption peak is found in an oscilloscope, the current is finely tuned under the condition that the temperature is controlled to be unchanged, and the locking of a gas detection peak wavelength is achieved (if accurate detection gas sensitive wavelengths are required to be obtained, the lasers may be connected to a wavelength meter, so that sensitive wavelengths can be obtained). After the sensitive wavelengths are locked, laser beam combination is achieved at a beam combiner (the purpose of beam combination is to reduce cost and simplify the gas component detection system, thereby achieving sharing of one gas chamber). The laser is detected by a detector at the end after multiple refractions in the gas chamber (the purpose of multiple refractions of the laser in the gas chamber is to prolong the path of light in gas detection, improve the precision and avoid errors caused by non-uniform distribution of the gas). The detector transmits detected signals to lock-in amplifiers corresponding to the respective gases, and the lock-in amplifiers achieve the extraction of each harmonic signal. An extracted second harmonic signal has a voltage amplitude signal directly proportional to measured concentration. The inversion of a relationship between the voltage amplitude signal and the concentration is completed before real-time monitoring, second harmonic voltage amplitude signals processed by the lock-in amplifiers are transmitted to a computer, and online real-time monitoring of a natural gas methane number can be achieved through calculation of a concentration and methane number relational expression.

A methane number online real-time monitoring system includes a laser tuning system, a gas component detection system and a data processing system. The laser tuning system includes a computer, laser drivers, tunable lasers, a laser beam combiner, a collimator, and a beam expander, which are connected in sequence. The gas component detection system includes a gas supply system pipeline, a hose, a valve, and a gas chamber, the gas supply system pipeline is connected with the gas chamber through the hose, and the valve is arranged on the hose. The data processing system includes a detector, lock-in amplifiers, an oscilloscope, and a data acquisition card, which are connected in sequence. One end of the gas chamber is connected with the beam expander, and the other end is connected with the detector. One end of the computer is connected with the laser drivers, and the other end is connected with the data acquisition card. The tunable lasers include a methane laser, an ethane laser, a propane laser, a butane laser, a carbon dioxide laser, and a nitrogen laser. The tunable lasers and the laser drivers are in one-to-one correspondence.

The methane number online real-time monitoring system of the disclosure is mainly composed of a computer, laser drivers, tunable lasers, a laser beam combiner, a collimator, a beam expander, a gas supply system pipeline, a valve, a plastic hose, a gas chamber, a detector, lock-in amplifiers, an oscilloscope, a data acquisition card, a clamp and the like. The methane number online real-time monitoring system is characterized in that the computer, the tunable lasers, the laser drivers, the laser beam combiner, the collimator, and the beam expander form a laser tuning system. The gas supply system pipeline, the plastic hose, the valve, and the gas chamber form a gas component detection system. The detector, the lock-in amplifiers, the oscilloscope, the data acquisition card, and the computer form a data processing system. Natural gas in the gas supply system pipeline is filled into the gas chamber after passing through the plastic hose through a gas valve. After the tunable lasers, the laser drivers, the laser beam combiner, the collimator, the beam expander, the detector, the oscilloscope, the computer, and the lock-in amplifiers are connected, temperature is roughly tuned and controlled to be unchanged, then current is accurately tuned, and a wavelength corresponding to a gas absorption peak is found. As the monitoring of the methane number involves six components, namely methane, ethane, propane, butane, carbon dioxide, and nitrogen, the six components need to be tuned so that a tuned wavelength is the wavelength at the gas absorption peak. After tunable laser passes through the gas chamber and absorbs energy, signals are captured by the detector and then modulated and demodulated by the lock-in amplifiers; second harmonic voltage amplitude signals directly proportional to measured gas concentration are output; the voltage amplitude signals are inverted by the computer to obtain the measured concentration; concentration signals of all the components are collected and input into a methane number and concentration calculation expression; and the measured methane number is displayed on the computer. Due to sharing of one gas chamber, laser beams with different wavelengths are combined when gas concentration monitoring of each component is achieved, one detector is shared, and time-sharing detection is achieved. This operation not only achieves simplification of the monitoring system, but also reduces the cost.

In summary, the methane number online real-time monitoring system provided by the disclosure includes a methane laser, an ethane laser, a propane laser, a butane laser, a carbon dioxide laser, a nitrogen laser, drivers for respective tunable lasers, a laser beam combiner, a gas chamber, a gas supply system pipeline, a plastic hose, a gas valve, a detector, lock-in amplifiers, a computer, an oscilloscope, a collimator, a beam expander, a clamp and the like. In a working process, the methane number online real-time monitoring system may monitor the natural gas methane number in real time online with high reaction rate. The methane number online real-time monitoring system meets the working requirements of natural gas engines, is convenient to carry, may monitor different engines in real time, and is free of post-processing and post-maintenance, easy to operate, and low in cost. The methane number online real-time monitoring system is high in severe environment adaptability, safe and reliable.

What is claimed is:

1. A system, comprising:
    a gas chamber, a computer, laser drivers, tunable lasers, a laser beam combiner, a collimator, a beam expander, a detector, and lock-in amplifiers;
    wherein the laser drivers are configured to tune wavelengths of the tunable lasers by changing temperatures and electric currents of the tunable lasers;
    wherein the laser beam combiner is configured to combine laser beams from the tunable lasers to form a combined laser beam;
    wherein the collimator is configured to collimate the combined laser beam and direct the combined laser beam to the beam expander;
    wherein the beam expander is configured to expand and direct the combined laser beam into the gas chamber;
    wherein the detector is configured to output, to the lock-in amplifiers, a signal representing the combined laser beam that has been refracted by a gas in the gas chamber;
    wherein the lock-in amplifiers are configured to extract amplitudes of the wavelengths from the signal and feed the amplitudes to the computer; and
    wherein the computer is configured to determine a methane number of the gas based on the amplitudes.

2. The system according to claim 1, wherein the wavelengths comprise peak absorption wavelengths of methane, ethane, propane, butane, carbon dioxide, and nitrogen.

3. The according to claim 1, wherein the tunable lasers and the laser drivers are in one-to-one correspondence.

* * * * *